United States Patent [19]

Imlah

[11] 4,407,164

[45] Oct. 4, 1983

[54] IMPART MACHINE FOR DETERMINING HEAT SETTING CONDITIONS

[75] Inventor: Forbes Imlah, Clarksville, Va.

[73] Assignee: Burlington Industries, Inc., Greensboro, N.C.

[21] Appl. No.: 394,438

[22] Filed: Jul. 1, 1982

[51] Int. Cl.³ .................. G01N 3/08; G01N 33/36
[52] U.S. Cl. .................................. 73/831; 73/159; 374/49
[58] Field of Search .................. 73/159, 826, 831; 26/70; 374/49

[56] References Cited

U.S. PATENT DOCUMENTS

| | | | |
|---|---|---|---|
| 1,211,598 | 1/1917 | Lake | 73/831 |
| 2,568,731 | 9/1951 | Hansen et al. | |
| 3,316,757 | 5/1967 | Fletcher | 73/831 |
| 3,329,010 | 7/1967 | Fryfogle et al. | |
| 3,400,576 | 9/1968 | Siciliano | |
| 3,444,728 | 5/1969 | Burns | |
| 3,528,145 | 9/1970 | Troope et al. | |

*Primary Examiner*—S. Clement Swisher
*Attorney, Agent, or Firm*—Cushman, Darby & Cushman

[57] ABSTRACT

A device for assisting in the prediction of the effects that a treatment, e.g. heat-setting, will have upon a textile fabric comprises a frame which defines an interior area, securing members for securing a textile fabric to the frame so as to cover the interior area, and an angularly displacable portion of the frame to vary the dimensional characteristic of the interior area so as to impart proportional and varying tension and extension to the fabric thereby aiding in the determination of the effects of the treatment thereon over a wide range of tension and extension parameters. The fabric is positioned on the frame, the frame is angularly displaced a predetermined amount and subsequently treated, and the treatment's effect are determined.

14 Claims, 4 Drawing Figures

U.S. Patent     Oct. 4, 1983     4,407,164

IMPART MACHINE FOR DETERMINING HEAT SETTING CONDITIONS

BACKGROUND AND SUMMARY OF THE INVENTION

The present invention generally relates to a novel device which aids in the accurate prediction of the effects that fabric treatments, for example, heat setting, will have upon a textile fabric. More particularly, the present invention relates to a device which can be utilized to simultaneously determine in one operation what effects will be exhibited by the textile fabric under an infinite variety of heat setting conditions, for example, the effects upon the fabric stretch, growth and shrinkages as these properties relate to varying fabric widths.

The device of the present invention generally comprises a frame which defines an interior area. The fabric material to be tested is placed on the frame and secured thereto by suitable means. At least one portion of the frame is pivotably attached to the remainder thereof so that an angular displacement can be effected to proportionally stretch the fabric yarn.

For example, in a preferred embodiment of the present invention, the frame comprises three elongated members, two of which are rigidly attached to one another to form an L-shaped side of the frame while the other member is pivotably attached to one of the L-shaped members thereby providing a "pivot arm". A turnbuckle or other suitable means is pivotably attached to the frame across the open end of the interior area defined by the L-shaped portion and the other pivotable frame member. Thus, upon operation of the turnbuckle, the pivot arm of the frame will be displaced angularly with respect to the fixed L-shaped frame member. In such a manner, proportional stretching of the fabric will occur, the fabric adjacent the turnbuckle portion being stretched more while the fabric adjacent the opposite end thereof being stretched to a lesser degree.

While in a stretched condition, the frame and fabric can be subjected to a variety of treatments, such as, heat treatments, and the fabric can thereafter be removed and examined to determined what effect varying degrees of tension have upon the fabric under the test conditions. Therefore, an accurate, and reliable laboratory prediction of the effects of heat setting conditions upon varying widths of fabric and under varying degrees of tension can be established so as to optimize production heat setting conditions in the textile mill.

According to prior practice, whenever heat setting conditions were desired to be determined and therefore, a stretch/heat setting relationship was required to be established, such determinations were accomplished on a "trial and error" basis by treating short yardages of fabric through the heat setter in production. Besides being a trial and error method, which often required many repetitions, this prior method was fairly tedious and unreliable as the short lengths and/or yardages used did not accurately represent or correlate production yardages that were treated. Accordingly, those in the art have endeavored to find suitable means for accurately and reliably predicting the effects upon fabric of heat setting conditions in a laboratory environment without resort to the trial and error basis using production equipment. It is believed that even though the need for such means was apparent, until the present invention, this need went unanswered.

There are, of course, prior art machines which can be utilized to test the physical characteristics of fabrics as exemplified by U.S. Pat. Nos. 2,568,731; 3,329,010; 3,404,576; 3,444,7288; and 3,528,145. However, such prior art devices are unsatisfactory for the particular relationships sought to be determined by utilizing the present invention, for example, the effects of heat setting upon an infinite variety of heat setting conditions and/or fabric.

For example, U.S. Pat. No. 2,568,731 discloses that a frame having two sides which are movable perpendicularly with respect to its associated, opposite fixed side can be utilized to determine stretch and recovery characteristics of the fabric. U.S. Pat. No. 3,329,010 discloses a portable device for conducting "grab tests" upon dryer-felts which may be applied to any portion of the dryer-felt while it is still upon the production machine. U.S. Pat. No. 3,400,576 and U.S. Pat. No. 3,444,728 each are concerned with determining the amount of stretch in fabric samples, while U.S. Pat. No. 3,528,145 is concerned with an apparatus for moving uniformly stretching fabrics in a cross-machine direction in order to determine when splits or cracks will occur in the fabric being stretched.

According to the present invention, however, there is provided a novel device which can be used in a laboratory environment to aid in the determination of optimum production settings for production machinery in view of the heat-setting effects upon the fabric being tested. According to the present invention, any fabric can be utilized and tested thereon, but it has been found that the present invention is particularly helpful in determining heat-setting effects upon stretchable fabrics, such as, lycra. In addition, the present invention can be utilized to predict production conditions for "bulking" fabrics having fibers which shrink in dry heat.

According to the present invention, therefore, a device is provided which is portable and can be placed in a laboratory oven to simulate production heat-setting conditions. The device according to the present invention generally comprises a frame which defines an interior area, a plurality of pins spaced along the perimeter of the frame so as to secure the textile fabric to the frame in the interior area defined thereby, and suitable means for displacing at least a portion of the frame angularly so that a portion of the fabric on the frame will be stretched to a greater degree than the fabric at another portion of the frame. Accordingly, the device according to the present invention provides a means for simultaneously simulating a variety of stretched conditions for the fabric and, subsequently, the frame having such fabric stretched thereon can be treated as desired to determine what effects such treatment will have on the fabric. Thus, since variations in the amount of tension and extension of the fabric will simultaneously be effected by utilizing the device according to the present invention, a clear and accurate understanding of the effects of various fabric treatments, such as, for example, heat-setting, can be achieved.

These and other advantages of the present invention will become more clear after careful consideration is given to the detailed discussion of the preferred exemplary embodiments thereof which follows.

BRIEF DESCRIPTION OF THE ACCOMPANYING DRAWINGS

Reference will be made to the accompanying drawings wherein.

DETAILED DESCRIPTION OF THE PREFERRED EXEMPLARY EMBODIMENTS

As noted above, the present invention is utilized in conjunction with testing procedures so that accurate and reliable determinations of the effects that certain fabric treatments will have upon the fabric being tested can be established. For example, the present invention can be utilized as an aid in predicting the heat-setting effects upon textile fabrics. However, although reference will be or has been made to "heat-setting" treatment, it will, of course, be appreciated that the present invention can be utilized to determine the effects of other fabric treatments such as, for example, dyeing, sizing, or drying operations. It has however been found to be particularly suitable for determining heat-setting conditions and, therefore, although reference is made to heat-setting treatment, those in the art will appreciate that such a reference is merely exemplary of a preferred embodiment according to the present invention and is therefore nonlimiting.

Figure 1:
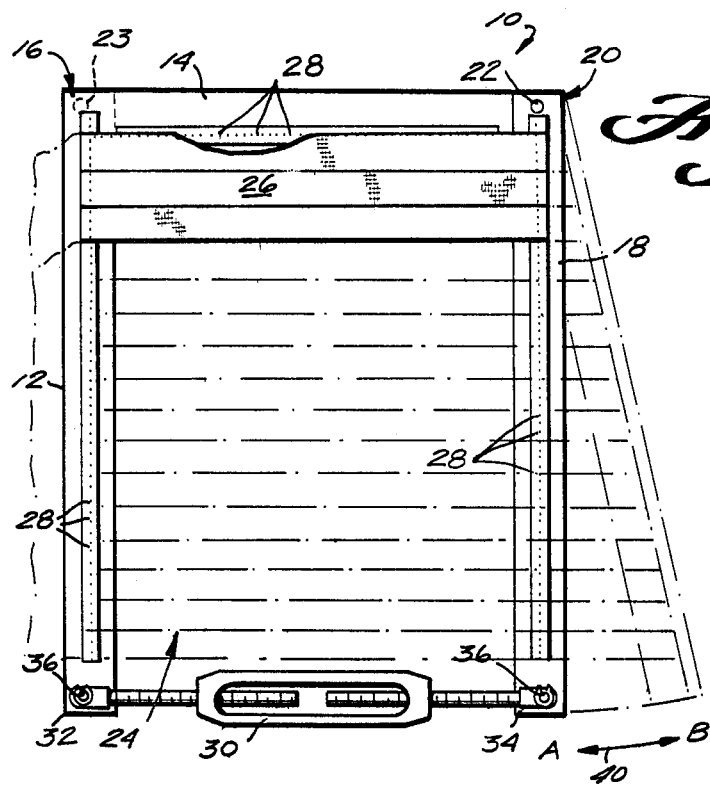
FIG. 1 is a plan view of an embodiment of the impart machine according to the present invention.

A preferred exemplary embodiment of the device 10 according to the present invention is depicted in FIG. 1. Generally, the device 10 according to the embodiment depicted in FIG. 1 comprises first and second frame members 12, 14, fixedly attached to one another at one end 16 and a pivotal arm 18 attached to the other end 20 of frame member 14 via pivot pin 22. In its rest position (noted by solid line in FIG. 1), device 10 generally defines a rectangular interior area 24 over which fabric material 26 can be placed. Fabric 26 is preferably secured to frame members 12, 14 and swing arm 18 by a plurality of elongated pins 28 which are disposed about the perimeter of the frame. Pins 28 penetrate the fabric 26 and therefore hold it securely in place.

A turnbuckle 30 is preferably provided to displace swing arm 18 and thereby stretch fabric 26 secured to device 10. The turnbuckle is pivotably attached to ends 32, 34 of frame member 12 and swing arm 18, respectively via pivot pins 36. A turnbuckle 30 is, of course, well known in the mechanical arts for tensioning guy wires or the like. However, according to the present invention, turnbuckle 30 is utilized in combination with swing arm 18 so as to displace swing arm 18 (noted in phantom line in FIG. 1) and therefore stretch fabric 26 bridging interior area 24. Thus, turnbuckle 30 can be manipulated (arrow 40) so as to move swing arm 18 to position B and, due to the nature of turnbuckle 30, swing arm 18 will remain in its displaced position until it is desired to return it to position A. Of course, other suitable state of the art devices can be utilized to displace swing arm 18 such as, hydraulic systems, electromechanical systems, or the like. Turnbuckle 30 in combination with the frame according to the present invention, however, is presently preferable since it is a reliable and inexpensive means for displacing swing arm 18.

Once swing arm 18 has been displaced by manipulating turnbuckle 30, (e.g. swing arm 18 is angularly displaced a predetermined angular distance so that the fabric adjacent to turnbuckle 30 is stretched greater than the fabric adjacent to frame member 14), device 10 can be placed in a suitable heat-setting oven, for example, a laboratory oven and subjected to a selected heat-setting condition. After the elaspe of a predetermined amount of time in the laboratory oven, frame 10 can be withdrawn, turnbuckle 30 manipulated so as to retract swing arm 18 from its angularly displaced position (e.g. move arm 18 from position B to position A) and fabric 26 can be marked and measured to determine the effects that the selected heat-setting condition had upon it.

The embodiment according to FIG. 1 can also be provided so that both members 12 and 14 are pivotably attached (e.g. by pivot pin 23 noted in dashed line in FIG. 1) to one another at end 16 similar to the manner in which swing arm 18 is pivotably attached at end 20 as already discussed. Thus, upon manipulation of turnbuckle 30 varying angular stretching and tensioning effects will be imparted to fabric 26 by virtue of both members 12 and 14 being angularly displaced relative to one another.

Figure 2:
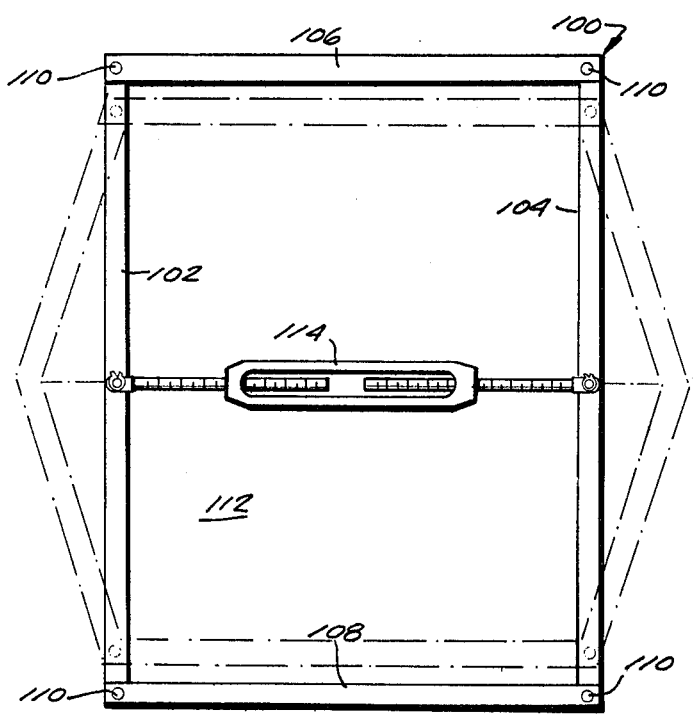
FIG. 2 is a plan view of another embodiment of the impart machine according to the present invention.

Another embodiment according to the present invention is depicted in FIG. 2 wherein the frame 100 is rectangular in shape having two pairs of opposing frame members each being pivotably attached to one another at their respective end portions. Opposing frame members 102, 104 are therefore pivotably attached to the second opposing pair of frame members 106, 108 by way of pivot pins 110. In a manner similar to the embodiment according to the present invention described in FIG. 1, an interior space 112 is defined by frame 100 over which a fabric (not shown for clarity of presentation) can be placed or secured in any suitable fashion such as, for example, utilizing elongated pins (not shown) around the perimeter of frame 100 (for reference, see pins 29 of FIG. 1).

Turnbuckle 114 is preferably disposed approximately midway between frame members 102 and 104 and is pivotably attached thereto so that frame members 102 and 104 are capable of pivotal movement (noted by phantom line in FIG. 2) upon manipulation of turnbuckle 114 to angularly displace frame members 102 and 104. Frame members 102, 104 are therefore displaced outwardly and angularly with respect to frame members 106, 108 by virtue of pivot pins 110.

Of course, it is conceivable that only one of frame members 102 or 104 can be pivotably displaceable at its midpoint while the other member is rigid along its entire length between its associated pivot pins 110. In such a manner and similar to the embodiment described in FIG. 1, various tensioning and extension characteristics will be imparted to the fabric so that the effect of varying heat-setting conditions can be determined thereon. Of course, turnbuckle 114 can be disposed between members 102, 104 other than at the midpoint thereof so that other stretch conditions can be established.

Figure 4:
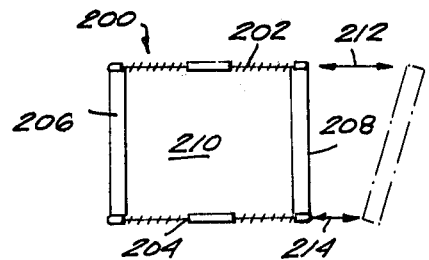
FIG. 4 is a schematic representation of another embodiment of the impart machine according to the present invention.

Referring more specifically to FIG. 4 wherein another embodiment according to the present invention is depicted, it is seen that a pair of opposing turnbuckles 202, 204 are pivotably attached to opposing frame members 206, 208 and together define interior area 210. Turnbuckles 202 and 204 can be manipulated independently of one another so that varying tensioning and extension characteristics can be imparted to the fabric (not shown for clarity in FIG. 4). Accordingly, it is conceivable that turnbuckle 22 can be manipulated (arrow 212) to a greater extent than the manipulation (arrow 214) of turnbuckle 204 so that the area or the fabric adjacent turnbuckle 202 will be tensioned and extended to a greater extent than the fabric adjacent to turnbuckle 204 (noted by phantom line in FIG. 4). Of course, the opposite may also be effected as well as equal manipulation of turnbuckles 202, 204.

The fabric which can be tested can be selected from any production area between the loom and the heat-setting operation. For example, the fabric to be tested can be selected from the production line immediately prior to heat-setting yet before dyeing; after scouring and air drying; or directly from the loom.

For the discussion which follows, reference will be made to the embodiment depicted in FIG. 1. However, the following discussion is similarly applicable to the other embodiments of the present invention discussed above.

Figure 3:
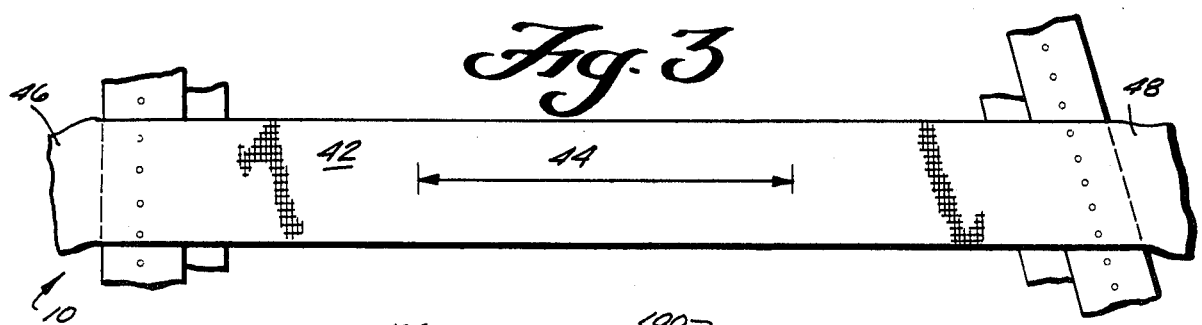
FIG. 3 is a detailed plan view showing a portion of the fabric under a stretched or "imparted" condition.

Once frame 10 having the fabric 26 thereon is removed from the laboratory oven and the turnbuckle 30 is manipulated to draw arm 18 into its retracted position (position A), the fabric is prepared for measuring to determine the effects that the selected heat-setting conditions had upon it. The fabric 26 is preferably cut into two inch strips along lines which were premeasured prior to placing the frame 10 into the heat-setting oven. Referring to FIG. 3, a strip of the fabric which has been marked and is shown on frame 10 is exemplary for the discussion which follows.

Fabric strip 42 which is preferably about 2 inches wide is marked for stretch testing using suitable widths (e.g. arrow 44) of 5-10 inches which are within the areas treated within the frame pins and not overlapping into "untreated" areas (e.g. fabric ends 46, 48). That is, the widths (arrow 44) which are marked for stretch testing appear on that portion of fabric strip 42 which was disposed over interior area 24. The "untreated area" is that area 46, 48 which overlaps frame 10 and, therefore, is not subject to the stretching action of arm 18 being angularly displaced by virtue of turnbuckle 30. Accordingly, no data can be obtained from "untreated areas" 46, 48 and they merely represent surplus fabric not involved in any subsequent testing.

After the strips 42 have been marked for stretch testing (arrow 44) they are steamed for 2 minutes to simulate the stock dyed routine where pieces are sponged during dry finishing, for example. During the steaming operation, the fabric is not under tension as it would restrict shrinkage. For piece dyes, the strips are boiled for approximately 30 minutes with gentle agitation, then steamed for about 2 minutes. With many fabrics, steaming only is close to conditions arrived at by boiling and steaming, but boiling has been found to be more closely parallel to dyeing conditions for resultant physical attributes.

The two inch strips are subsequently marked again for stretch testing using the 10 inch or 5 inch markings while preserving the original markings. It is imperative that during such subsequent testing that all markings must be sustained and preserved throughout the procedures and that all tests must be marked within the heat set areas. The strips are then measured for standard stretch/growth and shrinkage tests and the growth is subtracted out of the figures derived for shrinkage testing. The results are graphed on the basis of "impart percent" versus "stretch" and also "impart equivalent width" versus "impart related tension equivalent finished width".

When the above procedures are utilized, it has been found that reasonable and accurate results can be obtained, generally falling within 3 percent in stretch and an inch or so in width of the finished fabric, e.g. the finished production fabric. Variations in heat-setting within the laboratory oven are measured to maintain sufficiently close tolerances and the center of the laboratory oven being the area preferably used since it is the closest to the required conditions.

From the above procedures and test results, a variety of physical properties for an infinite variety of fabrics can be determined and forecast for finished fabric goods including, but not limited to, heat-setting conditions required during production; the finished stretch of the fabric; the finished width of the fabric; growth; shrinkage; weight per yard; and/or an assessment of finished appearance.

As can be appreciated, the present invention presents a novel device which can be utilized according to suitable laboratory procedures in order to evaluate the effects that various fabric treatments will have upon particular fabrics under a wide range of treatment settings. For example, when utilizing the embodiments according to the present invention, a variety of tensioning and extension characteristics can be imparted to the fabric being tested due to the angular displacement of the frame thereto. This factor in conjunction with the variety of conditions under which the fabric can be subjected will determine the optimum value for operating production machinery. Accordingly, the necessity for "trial and error" experimentation utilizing production machinery which would necessarily involve down time and therefore be nonproductive for such production machinery is completely obviated using the device according to the present invention.

The present novel device can also be utilized to determine or predict the conditions for "bulking" fabrics which contain fibers which shrink in dry heat. Utilizing "reverse impartation", the effects upon such "bulking" fabric can be predicted in a manner similar that described above. For example, when utilizing reverse impartation, the fabric is first placed upon the frame in its rest or substantially rectangular configuration and turnbuckle 30 is thereafter manipulated so as to draw in the impart arm angularly a predetermined amount. Thus, the bulking fabric will be loosely fitted over the interior are defined by the frame. Upon subjecting the frame and bulking fabric to dry heat, the fabric will stretch on the frame due to shrinkage of the bulking fabric. Thus, suitable determinations can be made to optimize and predict the production condition suitable for a high quality commercially viable product.

Thus, while the present invention has been herein described in what is presently conceived to be the most preferred embodiments thereof, those in the art will appreciate that many modifications may be made hereof which modifications shall be accorded the broadest scope of the appended claims so as to encompass all equivalent structures, devices and/or assemblies.

What is claimed is:

1. A device adaptable for assisting in the prediction of the effects that selected treatments will have upon textile fabric comprising:
   a frame defining an interior area;
   means for securing a textile fabric to said frame across said interior area; and impart means for angularly displacing at least a portion of said frame thereby varying the dimensional characteristic of said interior area.

2. A device as in claim 1 wherein said frame comprises first, second and third frame members, said first and second members being fixedly attached at one end of each thereof and said second and third members being pivotably attached at the other end of said second member, said impart means being operatively connected between said first and third members so that upon operation of said impart means, said third member is pivotably and angularly displaced relative said first and second members.

3. A device as in claim 1 wherein said frame comprises:
   first and second opposing pairs of frame members, at least one frame member of a predetermined one of said pairs pivotably connected at each end portion thereof to the respective end portions of the other of said pairs; and
   hinge means associated with said at least one frame member for permitting hinged movement of said at least one frame member intermediate said end portions, said impart means being disposed between said predetermined pair and operably connected to said hinge means.

4. A device as in claim 3 wherein the other frame member of said predetermined pair is pivotably connected to the other end portions of said other pair opposite said respective end portions, and includes second hinge means for permitting hinged movement of said other frame member intermediate said other end portions, said impart means being operably connected between said first mentioned hinge means and said second hinge means.

5. A device as in claim 3 or 4 wherein said impart means is disposed between said predetermined pair at substantially the midpoints of each.

6. A device as in claim 1 wherein said frame comprises first, second and third frame members, said first and third frame members at one end of each being pivotably connected to the opposing end portions of said second frame member, respectively, said impart means being operatively connected between said first and third members at the other end of each so that upon operation of said impart means, said first and third frame members are pivotably displaced relative said second frame member.

7. A device as in claim 1 wherein said frame comprises a pair of opposing frame members each having first and second opposing end portions, and wherein said impart means comprises first means connected between said first end portions of said pair for displacing said first end portions relative to one another, and second means connected between said second end portions of said pair for displacing said second end portions relative to each other.

8. A device as in claim 6 wherein said first and second means are separately operable.

9. A device as in claim 1, 2, 3, or 4 wherein said fabric securing means comprises a plurality of elongated pins disposed around the perimeter of said frame, each of said pins being spaced a predetermined distance with respect to adjacent ones.

10. A device as in claim 8 wherein said impart means comprises a turnbuckle.

11. A device for imparting varying tension to a fabric material so as to aid in the prediction of the effects that processing conditions will have upon the fabric material, said device comprising:
   a frame including an a L-shaped portion and an arm pivotably attached at one end to said L-shaped portion;
   securing means for securing a fabric material to said frame; and
   displacing means pivotably attached between the other end of said L-shaped portion and the other end of said arm for angularly displacing said arm relative said L-shaped portion so that varying tensioning conditions are effected upon said fabric material.

12. A device as in claim 11 wherein said L-shaped portion includes first and second frame members and pivot means connecting said first and second frame members.

13. A method of determining the effect that processing conditions will have upon a fabric material comprises the steps of:
   (a) selecting a device having a frame and means for angularly displacing at least a portion of said frame;
   (b) securing a fabric material to said frame;
   (c) angularly displacing said portion of said frame a predetermined amount to impart varying tension upon said fabric material; and
   (d) determining the effects of a predetermined process condition upon said fabric material.

14. A method as in claim 13 wherein step (d) is practiced by the steps comprising:
   (i) subjecting said fabric material to a predetermined processing condition and for a predetermined period of time;
   (ii) removing said fabric material from said processing condition after elapse of said predetermined time period; and
   (iii) measuring the effects of said processing condition upon said fabric material.

* * * * *